United States Patent
Antonacci

(10) Patent No.: US 8,634,071 B2
(45) Date of Patent: Jan. 21, 2014

(54) SYSTEM AND METHOD OF CLOSED CARTON INSPECTION

(75) Inventor: Steven Antonacci, East Syracuse, NY (US)

(73) Assignee: Steven R. Antonacci, Jamesville, NY (US)

(*) Notice: Subject to any disclaimer, the term of this patent is extended or adjusted under 35 U.S.C. 154(b) by 97 days.

(21) Appl. No.: 13/541,369

(22) Filed: Jul. 3, 2012

(65) Prior Publication Data

US 2013/0010298 A1    Jan. 10, 2013

Related U.S. Application Data

(60) Provisional application No. 61/504,622, filed on Jul. 5, 2011.

(51) Int. Cl.
    *G01N 21/00*      (2006.01)

(52) U.S. Cl.
    USPC .................. 356/239.4; 356/239.5; 356/239.6

(58) Field of Classification Search
    USPC ................................ 356/239.4, 239.5, 239.6
    See application file for complete search history.

(56) References Cited

U.S. PATENT DOCUMENTS

| | | | | |
|---|---|---|---|---|
| 3,454,759 A * | 7/1969 | Calhoun | .................... | 250/338.1 |
| 3,563,379 A * | 2/1971 | Stapf et al. | .................... | 209/524 |
| 5,155,019 A * | 10/1992 | Sussman et al. | ................. | 435/34 |
| 5,602,890 A * | 2/1997 | Gray et al. | ........................ | 378/57 |
| 5,864,600 A * | 1/1999 | Gray et al. | ........................ | 378/57 |
| 6,226,081 B1 * | 5/2001 | Fantone et al. | ............ | 356/239.6 |
| 6,473,170 B2 * | 10/2002 | Schafer | ....................... | 356/240.1 |
| 6,753,527 B1 * | 6/2004 | Yamagishi et al. | ...... | 250/339.06 |
| 8,037,659 B2 * | 10/2011 | Osborne et al. | ................... | 53/53 |

* cited by examiner

*Primary Examiner* — Roy M Punnoose
(74) *Attorney, Agent, or Firm* — Shimokaji & Assoc.

(57) ABSTRACT

An inspection of a closed carton for acceptable content fill may be provided by a transmitting unit and a receiving unit measuring intensity values of electromagnetic waves directed at the carton. A comparison of a reference intensity value to a measured intensity value may indicate whether the closed carton is filled correctly identifying missing contents such as the main product or a missing leaflet that may contain product instructions.

6 Claims, 3 Drawing Sheets

SYSTEM AND METHOD OF CLOSED CARTON INSPECTION

CROSS-REFERENCE TO RELATED APPLICATIONS

This application claims benefit under 35 U.S.C.§119(e) of U.S. Provisional Application having Ser. No. 61504622 filed Jul. 5, 2011, which is hereby incorporated by reference herein in its entirety.

BACKGROUND OF THE INVENTION

The present invention generally relates to packaging, and more particularly, a system and method of closed carton inspection.

A closed carton may be filled with packaging material that once packaged and sealed, is unavailable for visual inspection. For example, blister packs and a leaflet may be packaged for containers holding pharmaceutical products. It may be important to ensure all the contents are placed in the carton prior to final packaging. One known method for detecting missing contents of a closed carton is to weigh the carton on a weighing machine which method may not be able to detect missing items at full production speeds where cartons may be continuously moved on a conveyor belt mainly in part due to the very small weight difference a leaflet has in comparison to the overall weight differential of the product versus the leaflet. Another known method for detecting missing contents of a closed carton is by detecting eddy currents at the fill-height of metal parts which method may not be able to detect missing non-metallic items, such as leaflets.

As can be seen, there is a need for a system and method that can inspect cartons without visual inspection.

SUMMARY OF THE INVENTION

In one aspect of the present invention, a method of inspecting a closed carton comprises directing electromagnetic waves from an electromagnetic light source with a wavelength selected for the carton's transmission properties, at a height of a fill-line of a reference carton containing required elements at the fill-line; receiving electromagnetic waves penetrated through the reference carton by a receiving unit; determining a reference intensity value by the receiving unit; directing electromagnetic waves from the electromagnetic light source at a closed carton at the height of the fill-line of the reference carton; receiving electromagnetic waves penetrated through the closed carton by the receiving unit; determining a measured intensity by the receiving unit; comparing the measured intensity value with the reference intensity value; wherein if the intensity value is different from the reference intensity value, the closed carton does not contain the required element at the fill-line; and determining if the closed carton is correctly filled based on the comparison of the measured intensity value with the reference intensity value.

In another aspect of the present invention, a system of closed carton inspection comprises a micro-controller unit; a transmitting unit attached to the micro-controller unit including an electromagnetic light source capable of emitting electromagnetic waves of non-visible wavelengths; and a receiving unit attached to the micro-controller unit, spaced from the transmitting unit, the receiving unit capable of detecting electromagnetic waves emitted from the electromagnetic light source, wherein the microcontroller is configured to compare a measured intensity value of a closed carton passed between the transmitting unit and the receiving unit to a stored reference intensity value.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the disclosure. The description is not to be taken in a limiting sense, but is made merely for the purpose of illustrating the general principles of the disclosure, since the scope of the disclosure is best defined by the appended claims.

Broadly, an exemplary embodiment of the present disclosure provides a system and method of closed carton inspection, which may detect missing non metallic items such as leaflets. According to exemplary embodiments of the present disclosure, inspection of a closed carton is provided by scanning the closed carton with electromagnetic waves and comparing the intensity of transmitted electromagnetic waves of the closed carton with that of a reference carton.

Figure 1:
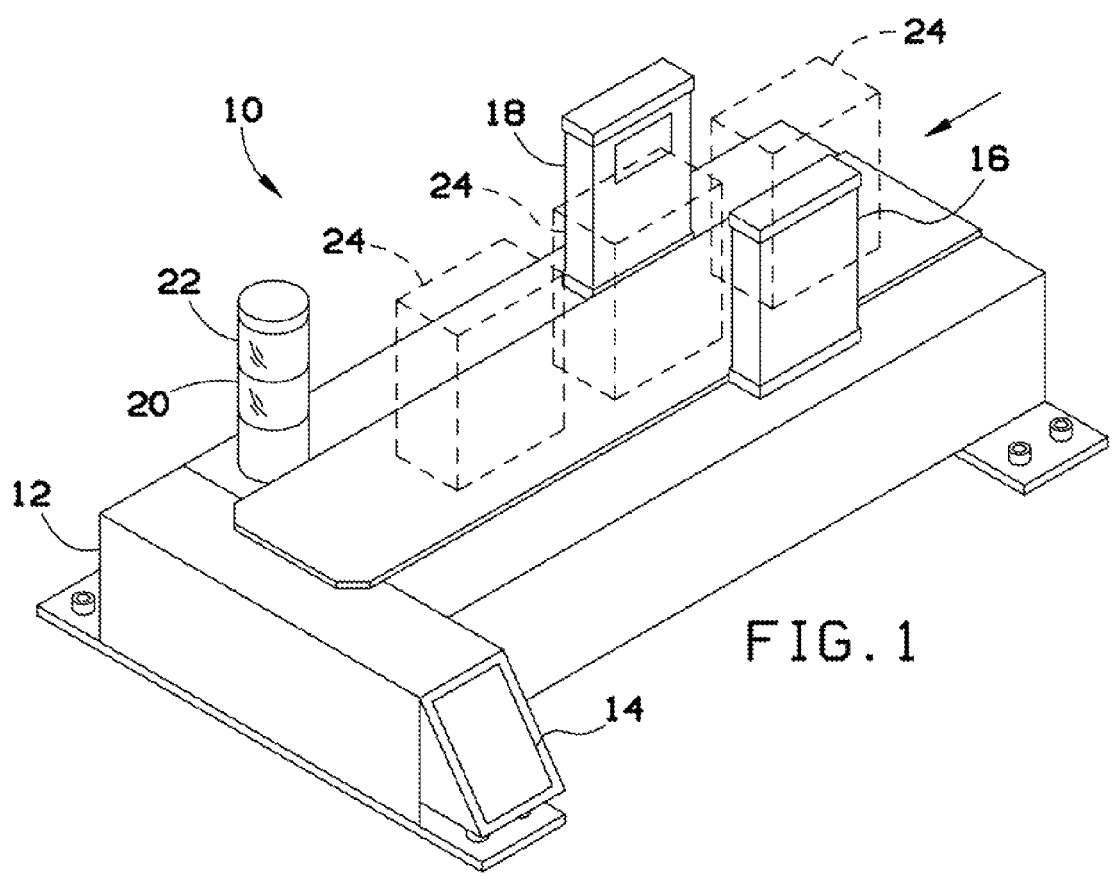
FIG. 1 is a schematic diagram of a system of closed carton inspection according to an exemplary embodiment of the present disclosure.

Referring now to FIG. 1, a system 10 of closed carton inspection is shown according to one or more embodiments of the present disclosure. The system 10 may include a micro-controller unit 12, a transmitting unit 16, and a receiving unit 18. The micro-controller 12 may be a computer, such as a PC, which is programmed to interface with an operator, the transmitting unit 16, and the receiving unit 18. The transmitting unit 16 and receiving unit 18 may be remotely controlled. The transmitting unit 16 may be an electromagnetic source providing a scanning output. The electromagnetic waves may be high powered electromagnetic waves having wavelengths in the non visible region according to one embodiment of the present disclosure. The electromagnetic source may be an infrared emitter configured to emit from near infrared to far infrared wavelengths. The wavelength emitted may be tuned based on the transmission properties of the carton to be inspected. The receiving unit 18 may be a receiver configured to detect output from the transmitting unit 16. The transmitting unit 16 may be spaced from the receiving unit 18 so closed cartons 24 may pass therebetween. An operator (not shown) may control the remote transmitting unit 16 and the remote receiving unit 18 through a touch pad 14 of the micro-controller unit 12. A pass signal indicator 20 and fail signal indicator 22 may be attached to the micro-controller 12 indicating respectively, whether an inspected closed carton 24 is filled correctly or not. In an exemplary embodiment, the pass signal 20 and fail signal 22 may be lights.

Figure 3:
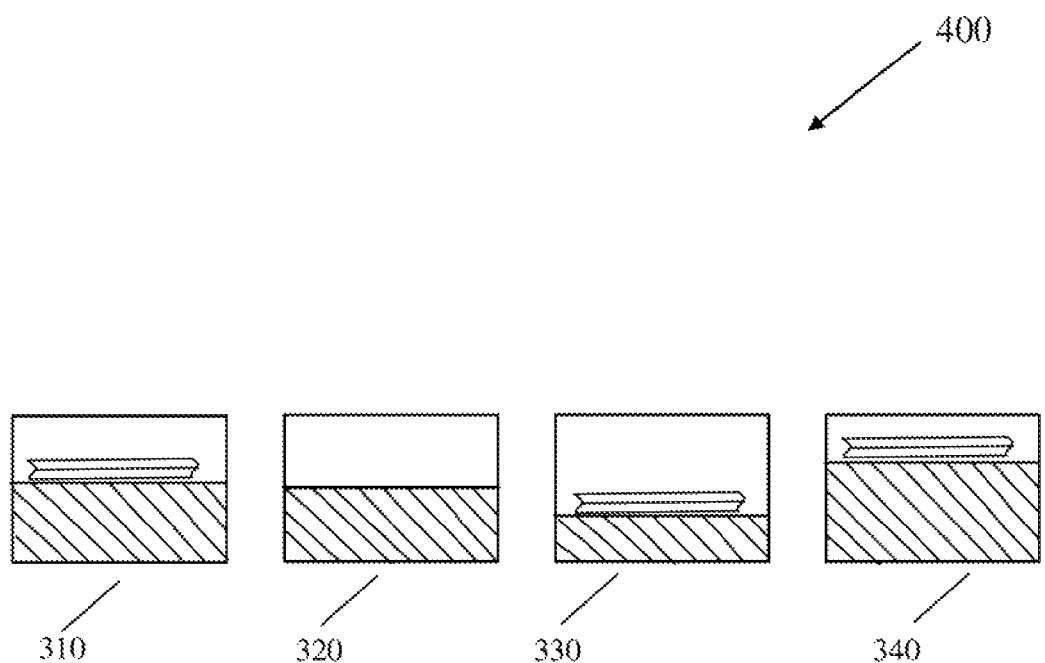
FIG. 3 is a side cross-sectional side view of an example of correctly filled closed carton and three examples of incorrectly filled closed cartons according to yet another exemplary embodiment of the present disclosure.

Referring now to FIGS. 1 and 3, closed cartons 24 may be placed between the transmitting unit 16 and receiving unit 18 when being inspected. A reference carton 310 having all the expected contents within a carton 24 may be scanned with electromagnetic waves from an electromagnetic light source inside the transmitting unit 16. The electromagnetic waves may be directed at a height of a fill-line of reference carton 310. The receiving unit 18 may receive electromagnetic waves penetrated through reference carton 310. The micro-controller 12 may calculate the intensity of the transmitted electromagnetic waves received by transmitting unit 18. The intensity of electromagnetic waves penetrated through reference carton 310 may be a reference intensity value, X, which may be input and stored in the micro-controller 12. Alternatively, the reference intensity value, X, may be a known value and may be input into the micro-controller directly, either by the operator or drawn from a database.

A carton 24 selected for inspection may be scanned with electromagnetic waves from the electromagnetic light source inside transmitting unit 16. The electromagnetic waves may be directed at a height of a fill-line of carton 24. In an exemplary embodiment, the electromagnetic source may flood the side of the carton with IR waves. Individual detectors may be in an array within the receiving unit 18. The detectors may be selected based on the desired fill height and the desired contents within the carton 24. Selection of the detectors may be performed through a combination of hardware and software analysis. An optimal number of detectors may based on the size of the carton and the expected beam spot through the carton 24. The infrared source can also be mechanically or electrically adjusted or masked for various box content applications. Receiving unit 18 may receive electromagnetic waves penetrated through the carton 24 and may calculate the intensity of the transmitted electromagnetic waves. The intensity of electromagnetic waves penetrated through the carton may be of an intensity value, Y, which may be input into micro-controller 12. The carton 24 may be stationary or may be continuously moving on a conveyor belt.

FIG. 3 shows examples of a reference carton 310 filled to an accepted correct fill-line with a leaflet on top. Further examples of closed cartons for inspection are shown as a closed carton 320 correctly filled but missing the leaflet; a closed carton 330 under filled below the fill-line; and a closed carton 340 over filled above the fill-line. It is important to not that in the case of a missing product but present leaflet, the leaflet can cover the missing product and the system will still detect the missing product because the emitter source will penetrate the leaflet.

Receiving unit 18 may receive more of the transmitting unit 16 electromagnetic wavelengths than that of reference carton 310, if the carton is more transparent than the reference carton in the scanned region which may indicate that the carton is either under filled or filled to the correct height but missing an additional item. The resulting intensity value Y would be greater than the reference intensity value X, according to one embodiment of the present disclosure. The intensity values received by the receiving unit 18 when closed cartons 320 and 330 are scanned may be greater than the reference intensity value, X. Closed cartons 320 and 330 may be rejected according to one embodiment of current disclosure.

Receiving unit 18 may receive less of the transmitted electromagnetic wavelengths than that of reference carton 310, if the carton is more opaque than the reference carton in the scanned region which may indicate that the carton is overfilled, for example, as may occur with carton 340. The resulting intensity value Y would be less than the reference intensity value X, according to one embodiment of the present disclosure.

The intensity value Y may be transmitted to micro-controller 12 by the receiving unit 18. Micro-controller 12 may compare the intensity value, Y, with the reference intensity value, X. The micro-controller 12 may turn on the pass signal light 22 if the intensity value Y corresponds to the reference intensity value X. The micro-controller 12 may turn on the reject light 20 if the intensity value, Y is not the same as the reference intensity value, X. According to one embodiment of the present disclosure, if Y is greater than X, then the carton may be rejected. If Y is less than X, this may indicate either an acceptably filled or overfilled condition which can result in a pass indication for proper filled. In some embodiments, an overfilled carton 24 may be failed. Failure due to overfill may be set according on setpoints provided on the micro-controller 12. Failed cartons 24 may invoke the micro-controller 12 to interface a rejection system.

Figure 2:
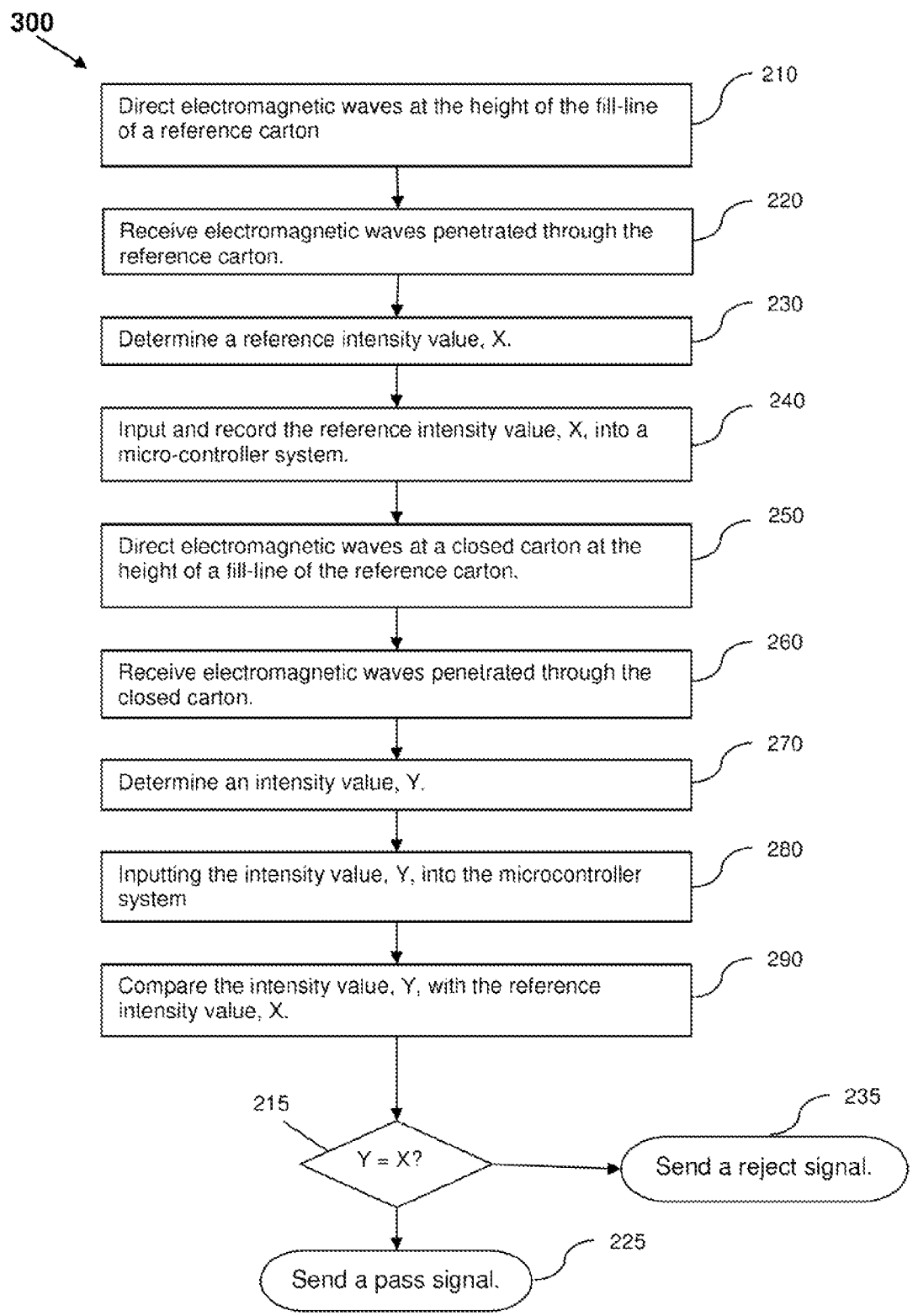
FIG. 2 is a flow chart of processes of closed carton inspection according to another exemplary embodiment of the present disclosure.

Referring to FIG. 2, a process 300 of inspecting a closed carton according to an exemplary embodiment of the present disclosure is shown. At step, 210, electromagnetic waves from an electromagnetic light source may be directed at a height of a fill-line of a reference carton containing a required element at the fill-line, for example, a leaflet. Electromagnetic waves penetrated through the reference carton may be received by a remote receiving unit at step 220. At step 230, a reference intensity value, X, may be determined by the remote receiving unit. The reference intensity value, X, may be input and recorded to a micro-controller system at step 240.

Electromagnetic waves from an electromagnetic light source may be directed at a closed carton selected for inspection at the height of the fill-line of the reference carton at step 250. Electromagnetic waves penetrated through the closed carton may be received by a remote receiving unit at step 260. At step 270, a measured intensity value, Y, may be determined by the remote receiving unit. The reference intensity value, Y, may be input to the micro-controller system at step 280.

At step 290, the micro-controller may compare the measured intensity value, Y, with the reference intensity value, X. If the intensity value, Y, corresponds to the reference intensity value, X, the closed carton may contain the required elements at the fill-line. The micro-controller may send a pass signal to the operator at step 225. If the intensity value, Y, is different from the reference intensity value, X, the closed carton may not contain the required element at the fill-line. The micro-controlled may send a reject signal to the operator at step 235.

It should be understood, of course, that the foregoing relates to exemplary embodiments of the invention and that modifications may be made without departing from the spirit and scope of the invention as set forth in the following claims.

I claim:

1. A method of inspecting a closed carton, comprising:
   directing electromagnetic waves from an electromagnetic light source at a height of a fill-line of a reference carton containing required elements at the fill-line;
   receiving electromagnetic waves penetrated through the reference carton by a receiving unit;
   determining a reference intensity value by the receiving unit;
   directing electromagnetic waves from the electromagnetic light source at a closed carton at the height of the fill-line of the reference carton;
   receiving electromagnetic waves penetrated through the closed carton by the receiving unit;
   determining a measured intensity by the receiving unit;
   comparing the measured intensity value with the reference intensity value; wherein if the intensity value is different from the reference intensity value, the closed carton does not contain the required element including missing leaflets at the fill-line; and determining if the closed carton is correctly filled based on the comparison of the measured intensity value with the reference intensity value.

2. The method of claim 1, including sending a pass signal to an operator if the measure intensity value is the same as the reference intensity value.

3. The method of claim 2 including sending a reject signal to the operator if the intensity value is different from the reference intensity value.

4. A system of closed carton inspection, comprising:
   a micro-controller unit;
   a transmitting unit attached to the micro-controller unit including an electromagnetic light source capable of emitting electromagnetic waves of non-visible wavelengths; and
   a receiving unit attached to the micro-controller unit, spaced from the transmitting unit, the receiving unit capable of detecting electromagnetic waves emitted from the electromagnetic light source, wherein the microcontroller is configured to compare a measured intensity value of a closed carton passed between the transmitting unit and the receiving unit to a stored reference intensity value.

5. The system of claim 4 further comprising a reject signal light attached to the micro-controller configured to indicate a fail signal when the measured intensity value is different than the reference intensity value and a control output to interface a rejection system.

6. The system of claim 5 further comprising a pass signal light attached to the micro-controller and a control output to indicate a pass signal when the measured intensity value corresponds to the reference intensity value.

\* \* \* \* \*